United States Patent [19]

Minagawa et al.

[11] 4,116,927
[45] Sep. 26, 1978

[54] 2,2,6,6-TETRAMETHYL-4-PIPERIDYL CARBOXYLIC ACID ESTERS OF BUTANE OR BUTENE TRI CARBOXYLIC ACIDS AS STABILIZERS FOR SYNTHETIC POLYMERS

[75] Inventors: Motonobu Minagawa, Kosigaya; Naohiro Kubota; Toshihiro Shibata, both of Urawa, all of Japan

[73] Assignee: Argus Chemical Corporation, Brooklyn, N.Y.

[21] Appl. No.: 812,968

[22] Filed: Jul. 5, 1977

[30] Foreign Application Priority Data

Jul. 12, 1976 [JP] Japan .................... 51-82024

[51] Int. Cl.² .............. C07D 211/44; C07D 211/46; C08K 5/34; C08K 5/35
[52] U.S. Cl. .............. 260/45.8 NZ; 260/45.8 N; 260/293.66; 260/293.88
[58] Field of Search ............ 260/45.8 N, 45.8 NZ, 260/293.66, 293.88

[56] References Cited
U.S. PATENT DOCUMENTS

| | | |
|---|---|---|
| 3,692,778 | 9/1972 | Murayama et al. ......... 260/45.8 NZ |
| 3,790,525 | 2/1974 | Murayama et al. ......... 260/45.8 NZ |
| 3,840,494 | 10/1974 | Murayama et al. ............ 260/293.88 |
| 3,875,169 | 4/1975 | Ramey et al. ................. 260/45.8 N |
| 3,899,464 | 8/1975 | Murayama et al. ......... 260/45.8 NZ |
| 3,993,655 | 11/1976 | Rasberger et al. ............. 260/45.8 N |
| 4,007,158 | 2/1977 | Murayama et al. ......... 260/45.8 NZ |
| 4,069,196 | 1/1978 | Ramey et al. ................. 260/45.8 NP |

OTHER PUBLICATIONS

Dictionary of Organic Compounds, 1953, vol. 3, pp. 520 and 521, and vol. 4, p. 555.

Primary Examiner—Donald E. Czaja
Assistant Examiner—R. A. White

[57] ABSTRACT

2,2,6,6-tetramethyl-4-piperidyl carboxylic acid esters of butane or butene tricarboxylic acids are provided, useful as stabilizers for organic polymeric materials, and having the general formula:

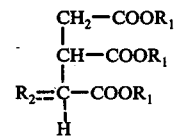

wherein:
$R_1$ is selected from the group consisting of

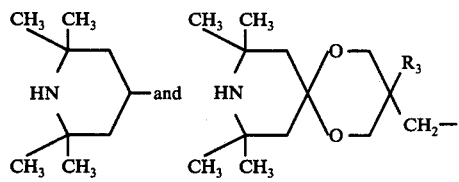

the $R_1$ groups can be the same or different;
$R_2$ is selected from the group consisting of $CH_3$ and $CH_2$; and
$R_3$ is lower alkyl.

18 Claims, No Drawings

2,2,6,6-TETRAMETHYL-4-PIPERIDYL CARBOXYLIC ACID ESTERS OF BUTANE OR BUTENE TRI CARBOXYLIC ACIDS AS STABILIZERS FOR SYNTHETIC POLYMERS

Hindered 2,2,6,6-tetraalkyl-4-carboxylic acid ester piperidine compounds have been proposed by Murayama et al U.S. Pat. No. 3,640,928 patented Feb. 8, 1972 as light and heat stabilizers for synthetic polymers, such as polyolefins, polyvinyl chloride, polyvinylidene chloride, polyurethanes, and polyamides. These compounds have the general formula:

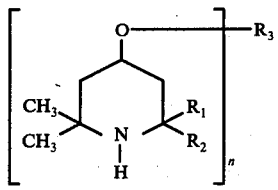

or a salt thereof.

In the above Formula:

$R_1$ and $R_2$ which may be the same or different, each are an alkyl group such as methyl, ethyl, isopropyl or dodecyl, or they form, together with the carbon atom to which they are attached, a saturated alicyclic group such as:

or a group of the formula

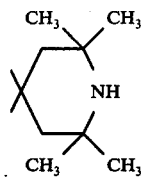

$n$ is an integer of 1 to 3 inclusive: and $R_3$ is an acyl group.

These compounds have proved to be particularly acceptable because they do not impart a discoloration of their own to the synthetic polymer. The compounds generally employed previously have either been highly colored, such as the nickel compounds (which are normally green) and the 2-hydroxybenzophenones (which are varying shades and intensities of yellow). They also show very little tendency towards sublimation and exudation, and they have an excellent stabilizing action against both heat and light deterioration.

Consequently, the Murayama et al patent has been followed by a large number of patent and literature disclosures by Murayama et al and others of compounds including a 2,2,6,6-tetrasubstituted-4-piperidyl group attached to a base molecule of varying structures.

Murayama et al U.S. Pat. No. 3,893,303 patented Aug. 5, 1975 propose piperidino-spiro-hydantoin derivatives having the formula:

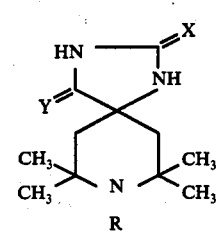

wherein

R represents an alkyl group, an alkenyl group, an alkenoyl group which may be substituted with an aryl group, a hydroxyalkyl group, an alkoxyalkyl group, an alkoxycarbonylalkyl group, an acyloxyalkyl group, a cyanoalkyl group or nitroso group, and X and Y individually represent oxygen atom or sulfur atom.

Murayama et al in U.S. Pat. No. 3,899,464 patented August 12, 1975 disclose a variation of the piperidino spiro compounds having the formula:

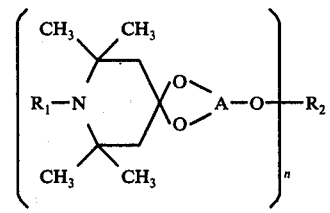

wherein $R_1$ represents hydrogen atom, an alkyl group, a substituted alkyl group, an alkenyl group, an alkynyl group, a substituted or unsubstituted aralkyl group, an aliphatic acyl group, an alkoxycarbonyl group or an aralkoxycarbonyl group, $n$ is an integer of 1 to 4;

When $n$ is 1, $R_2$ represents hydrogen atom, an aliphatic aromatic or heterocyclic monoacyl group, an alkyl group, an alkenyl group, an alkynyl group, an aralkyl group, an aryl group, an alkoxyalkyl group, an epoxyalkyl group, an alkoxysulfonylalkyl group, N-substituted carbamoyl group, a N-substituted thiocarbamoyl group, a monovalent group from an oxoacid or group

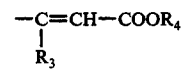

in which $R_3$ represents hydrogen atom, a lower alkyl group or phenyl group and $R_4$ represents an alkyl group;

when $n$ is 2, $R_2$ represents carbonyl group, an aliphatic or aromatic diacyl group, an alkylene group, an alkenylene group, an alkynylene group, an aralkylene group, a N-substituted dicarbamoyl group or a divalent group from an oxoacid;

when $n$ is 3, $R_2$ represents an aromatic triacyl group or a trivalent group from an oxoacid; and when $n$ is 4, $R_2$ represents an aromatic tetraacyl group, and A represents a group

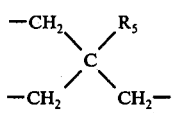

in which
R$_5$ represents hydrogen atom or a lower alkyl group or, when n is 1, R$_5$ may represent together with R$_2$ a group

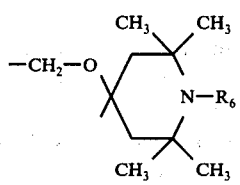

in which
R$_6$ represents the same group as defined in R$_1$ and may be the same or different from R$_1$, or a group

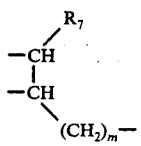

in which
m is 1 or 2 and R$_7$ represents hydrogen atom or, when n and m are 1, R$_7$ represents methylene group together with R$_2$.

Murayama et al U.S. Pat. No. 3,933,735 patented Jan. 20, 1976 propose 4-piperidone derivatives having a structure similar to the 4-piperidyl derivatives, but with a keto oxygen at the 4-position of the piperidine ring.

Murayama et al U.S. Pat. No. 3,941,744 patented Mar. 2, 1976, disclose another variation of the piperidino spiro derivatives having the formula:

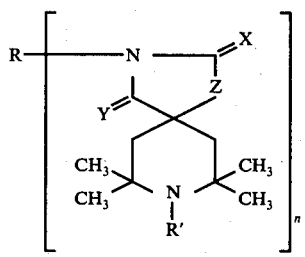

wherein
R' represents an alkyl group, a substituted alkyl group, an acyl group, an alkoxycarbonyl group, a substituted alkoxycarbonyl group, an amino group, a substituted amino group or nitroso group;

X represents oxygen atom or sulfur atom;

Y represents oxygen atom, sulfur atom or a group of the formula =N-R" in which R" is hydrogen atom, an alkyl group or a substituted alkyl group;

Z represents oxygen atom or a group of the formula >N-R''' is hydrogen atom, an alkyl group or a substituted alkyl group;

n is an integer of 1 through 4 inclusive; and

R represents, when n is 1, an alkyl group, a substituted alkyl group, an aryl group, a substituted aryl group, a cycloalkyl group, an alkoxycarbonyl group, a substituted alkoxycarbonyl group, a substituted phosphino group or a substituted phosphinyl group, when n is 2, an alkylene group, an alkenylene group, an arylene group, a substituted arylene group, an aralkylene group, an alkylenediphenylene group, a bis-(acyloxyalkylene) group, an alkylene-bis-(oxycarbonylalkyl) group, a dialkylene ether group or a diphenylene ether group, when n is 3, an alkanetriyl group, a tris(acyloxyalkylene) group, an alkane-tris-(oxycarbonylalkyl) group or a group of the group

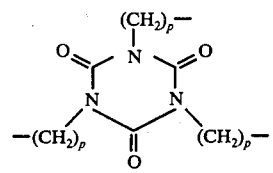

in which
p is an integer of 1 through 8 inclusive, and when n is 4, an alkane tetrayl group, a tetrakis-(acyloxyalkylene) group or an alkanetetrakis(oxycarbonylalkyl) group.

Murayama et al U.S. Pat. No. 3,940,363 patented Feb. 24, 1976 disclose a further variation in which two 2,2,6,6-tetrasubstituted-4-piperidyl groups are linked together via the ring nitrogen atom to an R' alkylene linking group, which may be interrupted with an oxygen or sulfur atom, an alkenylene group, an alkynylene group, an aralkylene group, an aliphatic diacyl group, a group having the formula:

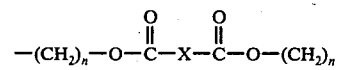

in which
n is an integer of 1 or 2 and X is an alkylene group, or o-, m- or p-phenylene group or the carbon atoms of CO groups may be directly joined in the absence of X or a group of the formula:

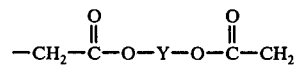

in which
Y is an alkylene group or o-, m- or p-phenylene group.

Ramey et al U.S. Pat. Nos. 3,899,491, patented Aug. 12, 1975 and 3,920,659, patented Nov. 18, 1975, disclose alkyl alkanoate derivatives of substituted piperazines and substituted piperazinodiones. The substituted piperazines of U.S. Pat. No. 3,899,491 have the formula:

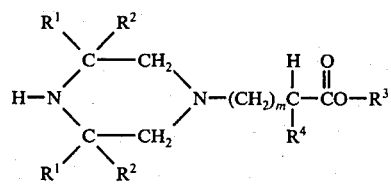

wherein
R$^1$ and R$^2$ are methyl or together with the carbon to which they are bound form a mono-cyclic ring system having five or six carbon atoms;

$R^3$ is an alkyl group of from one to twenty atoms;
$R^4$ is hydrogen or methyl, and
$m$ is 0 or 1.

The substituted piperazinodiones of U.S. Pat. No. 3,920,659 have the formula:

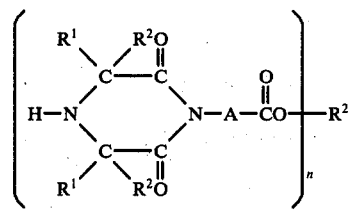

wherein $R^1$ and $R^2$ are independently of each other methyl or ethyl or together with the carbon to which they are bound form a cyclopentyl or cyclohexyl ring, which is unsubstituted or substituted with a methyl group;

$n$ is an integer of from 1 to 2;

when $n$ is 1, $R^3$ is an alkyl group of from one to twenty carbon atoms;

when $n$ is 2, $R^3$ is an alkylene group of from two to eight carbon atoms; and A is a straight or branched chain (lower) alkylene group containing from one to six carbon atoms with the limitation that the terminals of said alkylene group bear only hydrogen or one (lower) alkyl group.

Ramey et al U.S. Pat. No. 3,920,661 patented November 18, 1975 disclose dicarboxylic acids and salts in which one carboxylic acid group is esterified with a 2,2,6,6-tetrasubstituted-4-hydroxy piperidine and having the formula:

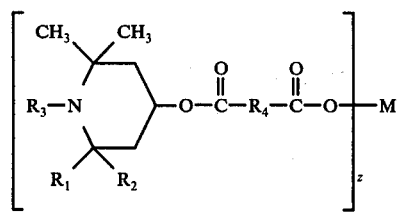

wherein $R_1$ and $R_2$ independently of each other are straight- or branchedchain alkyl having from one to six carbon atoms, or together with the carbon to which they are bound form a cyclopentyl or cyclohexyl ring, which is unsubstituted or substituted with a methyl group;

$R_3$ is hydrogen, alkyl having one to twelve carbon atoms, $\beta$-methoxyethyl, alkenyl having three or four carbon atoms, propargyl, benzyl or alkyl-substituted benzyl;

$R_4$ is straight or branched-chain alkylene having five to eight carbon atoms, or the group $(CH_2)_m Y(CH_2)_n$ wherein Y is oxygen or sulfur and $m$ and $n$ independently of each other are an integer from 1 to 3;

M is hydrogen or a metal selected from the group consisting of barium, nickel, manganese, calcium, zinc, iron, sodium, cobalt, tin, and dialkyl tin, and $z$ has a value of from 1 to 4, the value of $z$ being the same as the available valence of M.

Ramey et al U.S. Pat. No. 3,939,163 patented Feb. 17, 1976 disclose closely similar compounds in which $R_4$ is alkylene having from one to four carbon atoms.

Randell et al U.S. Pat. No. 3,939,170 patented Feb. 17, 1976 disclose dehydropyridinyl sulphides, sulphoxides and sulphones having the formula:

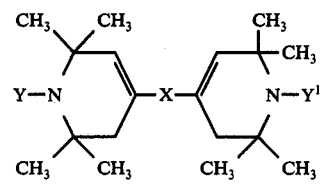

wherein

X is S, SO or $SO_2$ and Y and $Y^1$ are the same or different and each is H, OH, O— or a straight- or branched alkyl residue having from one to four carbon atoms, and salts thereof when Y and $Y^1$ are other than O-

Randell et al in published patent application No. B408,123 published Apr. 13, 1976 disclose substituted piperidine-4-ols having the formula:

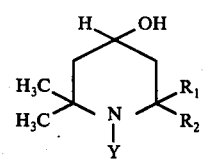

wherein $R_1$ and $R_2$ are the same or different and each is a straight- or branched alkyl residue having from one to twelve carbon atoms, or $R_1$ and $R_2$, together with the carbon atom to which they are attached, form a cycloalkyl residue having from five to twelve carbon atoms or the group:

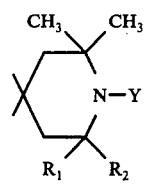

wherein $R_1$ and $R_2$ have their previous significance and Y is a straight- or branched alkyl residue having from one to twenty carbon atoms, an alkenyl or alkynyl residue having from three to twenty carbon atoms, an aralkyl residue having from seven to twelve carbon atoms or the group $—CH_2X$ wherein X is the group

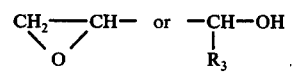

wherein $R_3$ is hydrogen, a methyl or phenyl residue, the group

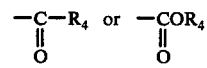

wherein $R_4$ is an alkyl residue having from one to twenty carbon atoms.

Cook U.S. Pat. No. 3,929,804 patented Dec. 30, 1975 discloses 4-piperidine acetamide compounds having the formula:

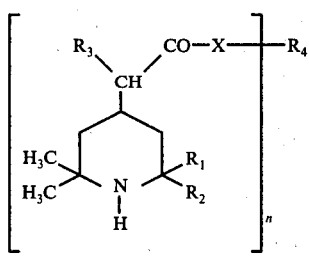

wherein $R_1$ and $R_2$ are the same or different and each is a straight- or branched alkyl residue having from one to twelve carbon atoms, or $R_1$ and $R_2$, together with the carbon atom to which they are attached form a cycloalkyl group having from five to twelve carbon atoms;

$R_3$ is hydrogen, a straight- or branched alkyl residue having from one to four carbon atoms, an aralkyl residue having from seven to nine carbon atoms or a cycloalkyl group having from five to six carbon atoms;

$R_4$ is a metal ion or a hydrocarbyl residue having from two to twenty carbon atoms and being either unsubstituted or substituted by halogen or interrupted by one or more oxygen or sulphur atoms;

X is $-O-$, $-S-$, or $>NR_5$, wherein $R_5$ has the same significance as $R_3$; and n is 2, 3 or 4; as well as salts of the amine function of the compounds of formula I.

Cook U.S. Pat. No. 3,939,168 patented Feb. 17, 1976 discloses closely similar compounds having a Y substituent on the piperidyl nitrogen atom, Y being alkyl, alkenyl, aralkyl or a group

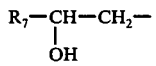

wherein $R_7$ is hydrogen, alkyl or phenyl.

In accordance with the instant invention, 2,2,6,6-tetramethyl-4-piperidyl carboxylic acid esters of butane or butene tricarboxylic acids are provided, useful as stabilizers for organic polymeric materials, and having the general formula:

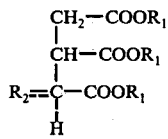

wherein $R_1$ is selected from the group consisting of

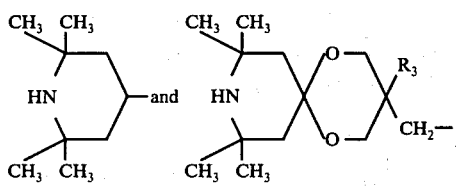

the $R_1$ groups can be the same or different;

$R_2$ is selected from the group consisting of $CH_3$ and $CH_2$; and $R_3$ is lower alkyl.

The $R_3$ alkyl has from one to about six carbon atoms. Exemplary are methyl, ethyl, n-propyl, isopropyl, n-butyl, isobutyl, tertiary butyl, secondary butyl, n-amyl, isoamyl, tertiary amyl, n-hexyl, isohexyl, secondary hexyl and tertiary hexyl.

The following compounds are exemplary:

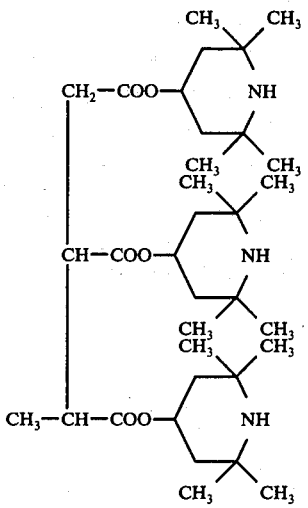

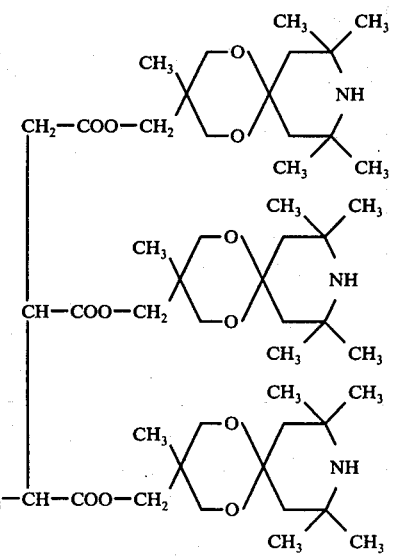

-continued

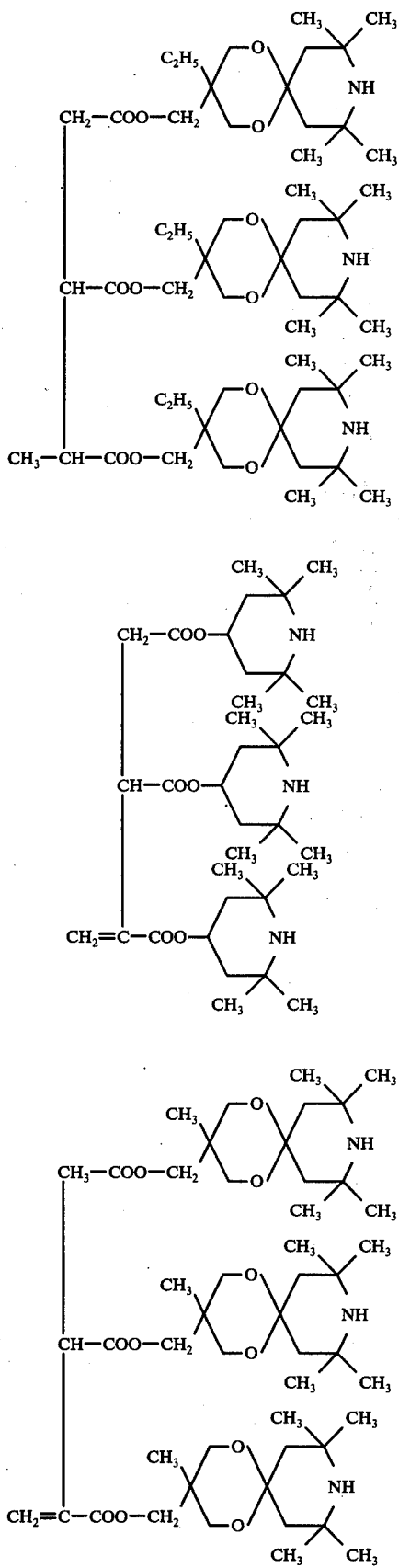

-continued

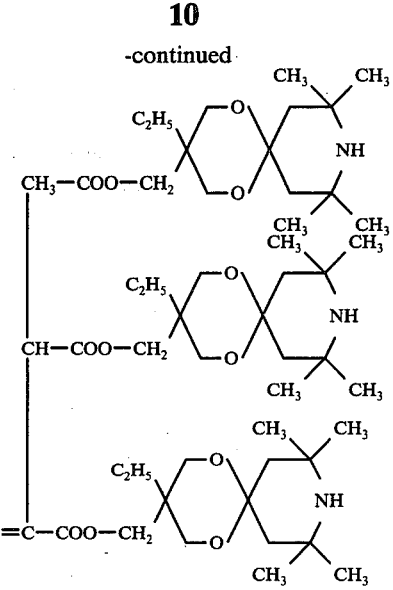

The compounds in accordance with the invention are readily prepared using conventional procedures. The starting materials are either available or readily synthesized without difficulty. The corresponding 2,2,6,6-tetra-substituted-4-hydroxy piperidine is used as a starting material for the 2,2,6,6-tetrasubstituted-4-piperidyl group $R_1$. This is reacted with one or more carboxylic acid groups of the corresponding butane or butene tricarboxylic acid or lower alkyl ester in the presence of an organic solvent and a suitable esterification or transesterification catalyst. The hydroxy group of the piperidine becomes esterified or transesterified with the carboxylic acid groups of the acid or ester, forming the 4-piperidinyl carboxylic acid ester of the invention:

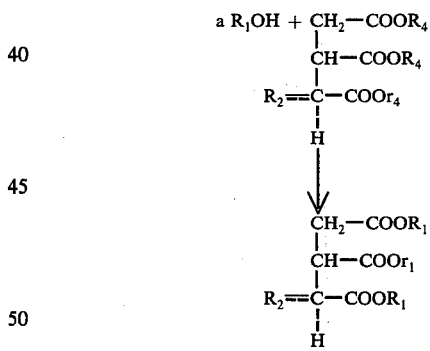

where $R_2$ is $CH_3$ or $CH_2$ and $R_4$ is H or lower alkyl such as methyl.

Suitable reactor temperatures are from about 90° to about 210° C. Transesterification catalysts can include alkaline materials such as an alkali or alkaline earth metal, which can be added in the form of the metal or in the form of an alkaline compound, such as an alkaline oxide or hydroxide, or alkaline salt, such as the carbonate or hydride, or as the alcoholate. Sodium is quite potassium carbonate, lithium hydroxide, potassium hydroxide, sodium hydride, lithium hydride, potassium hydride, calcium hydride, the oxides and hydroxides of calcium strontium and barium, and the alcoholates, usually of methyl, ethyl or isopropyl alcohol, or phenolates of all of these metals. Other metal alkoxides such as those of aluminum, titanium and zirconium can be used, as well as organotin compounds such as dibutyl tin oxide, dimethyl tin dilaurate, and dimethyl tin diacetate; and heavy metal salts such as cobalt naphthenate and lead 2-ethyl hexoate. Only a very small amount of the catalyst need be employed, for example, as little as from 0.01 to 2% by weight.

The following Examples illustrate the preparation of the compounds of the invention:

EXAMPLE I

Preparation of:

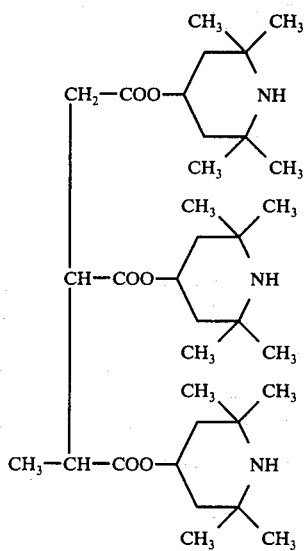

3.5 g of butane-1,2,3-tricarboxylic acid trimethyl ester, and 7.5 g of 2,2,6,6-tetramethylpiperidine-4-ol were dissolved in 60 ml of xylene, and 0.2 ml of titanium tetraisopropoxide added.

The solution was heated and stirred for 5 hours up to 140° C., while distilling off the methanol as it was liberated. After cooling, the solution was filtered, and 100 ml of ethyl ether was added to the filtrate. The resulting solution was washed with water, dried with K₂CO₃. A very pale yellow viscous liquid residue was obtained, after distilling off the solvent. White crystals m.p. 119°-121° C. were obtained by recrystallization of the viscous liquid from n-hexane.

| Elemental Analysis: | C% | H% | N% |
|---|---|---|---|
| Found: | 67.85 | 9.93 | 6.70 |
| Calculated: | 67.18 | 10.11 | 6.91 |
| IR Analysis: | | | |
| γNH: 3280 cm⁻¹ | γC: 1730 cm⁻¹, | δCH₃: 1380 cm⁻¹ | |

The product was shown by the analytical results to have the formula shown above.

EXAMPLE II

Preparation of:

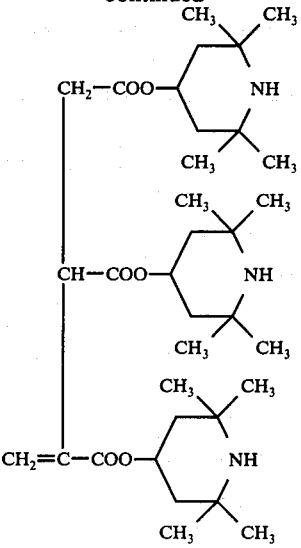

3-Butene-1,2,3-tricarboxylic acid trimethyl ester 4.6 g, and 9.9 g 2,2,6,6-tetramethyl-4-hydroxy piperidine were dissolved in 80 ml of xylene and 0.2 ml tetraisopropyl titanate was added. The solution was reacted for 5 hours at 140° C., while distilling off the methanol produced. The reaction mixture was cooled, and 200 ml ethyl ether added. The mixture was washed with water, dried, and the solvent removed by distillation. A pale yellow viscous liquid was obtained.

| Elemental Analysis: | C% | H% | N% |
|---|---|---|---|
| Found: | 68.14 | 9.65 | 6.73 |
| Calculated: | 67.40 | 9.82 | 6.94 |
| IR Analysis: | | | |
| γNH: 3280 cm⁻¹ | γC=O: 1725 cm⁻¹ | δCH₃: 1380 cm⁻¹ | |

The product was shown by these analytical results to have the formula shown above.

EXAMPLE III

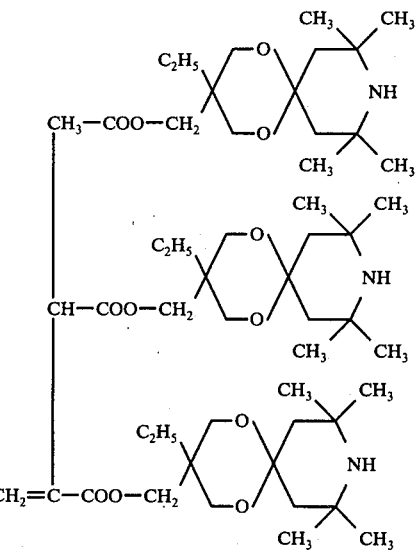

3-Butene-1,2,3-tricarboxylic acid trimethyl ester 4.6 g and 9-aza-3-ethyl-3-hydroxy methyl-8,8,10,10-tetramethyl 1.5-dioxaspiro [5.5] undecane 17.1 g were dissolved in 80 ml of xylene, 0.3 ml titanium tetra isopropoxide was added, and the reaction mixture was heated and stirred for six hours at 140° C. while distilling off methanol as it was liberated. After cooling, 200 ml of ethyl ether was added to the solution and the resulting solution washed with water, dried with $K_2CO_3$, and the ethyl ether removed by distillation, whereupon a pale yellow viscous liquid was obtained.

| Elemental Analysis: | C% | H% | N% |
|---|---|---|---|
| Found: | 66.03 | 9.69 | 4.31 |
| Calculated: | 65.65 | 9.75 | 4.42 |
| IR Analysis: | | | |
| $\gamma$NH: 3300 cm$^{-1}$ | $\gamma$C=O: 1720 cm$^{-1}$ | $\delta$CH$_3$: 1375 cm$^{-1}$ | |

The product was shown by these analytical results to have the formula shown above.

The 2,2,6,6-tetrasubstituted-4-piperidyl carboxylic acid esters of the invention are effective stabilizers to enhance the resistance to deterioration due to heat and/or light of synthetic polymeric materials which are susceptible to such degradation, including polyolefins such as low density polyethylene, high density polyethylene, polypropylene, polybutylene, polyisobutylene, polypentylene, and polyisopentylene, polystyrene; polydienes, such as polybutadiene and polyisoprene; and copolymers of olefins and dienes with other ethylenically and acetylenically unsaturated monomers, such as ethylene-propylene copolymers, ethylene-butene copolymers, ethylene-pentene copolymers, ethylene-vinyl acetate copolymers, styrene-butadiene copolymers, acrylonitrile-styrene-butadiene copolymers, synthetic rubbers of all types, such as polychloroprene; polyvinyl halides, including polyvinyl chloride homopolymer, polyvinylidene chloride; and copolymers of vinyl chloride and vinylidene chloride; vinyl chloride and vinyl acetate; vinylidene chloride and vinyl acetate; and other ethylenically unsaturated monomers; polyacetals such as polyoxymethylene and polyoxyethylene; polyesters such as polyethylene glycol-terephthalic acid ester polymers; polyamides such as polyepsiloncaprolactam; polyhexamethylene adipamide and polydecamethylene adipamide; polyurethanes; and epoxy resins.

The synthetic polymer can be in any physical form, including (for example) filaments, yarns, films, sheets, molded articles, latex, and foam.

The stabilizers of the invention can be employed as the sole stabilizer or, preferably, in combination with other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organic triphosphites, organotin compounds; hindered phenols; and epoxy compounds.

With polyolefin resins there can be employed fatty acid salts of polyvalent metals, organic phosphites, phenolic antioxidants, and the higher fatty acid esters of thiodipropionic acids, such as, for example, dilauryl thiodipropionate.

With polyamide resin compositions, polyamide stabilizers such as copper salts in combination with iodides and/or phosphorus compounds and salts of divalent manganese can be used.

With synthetic rubbers and acrylonitrile butadiene styrene terpolymers, antioxidants such as hindered phenols and bis-phenols, polyvalent metal salts of the higher fatty acids, and organic phosphites can be used.

In addition, other conventional additives for synthetic polymers, such as plasticizers, lubricants, emulsifiers, antistatic agents, flameproofing agents, pigments and fillers, can be employed.

The following Examples in the opinion of the inventors represent preferred embodiments of synthetic resin compositions in accordance with the invention.

EXAMPLES 1 to 6

Polypropylene compositions were prepared using stabilizers of the invention and three of the prior art, and having the following formulation:

| Ingredient | Parts by Weight |
|---|---|
| Polypropylene | 100 |
| Dilauryl thiodipropionate | 0.3 |
| Stearyl $\beta$-(3,5-di-t-butyl-4-hydroxyphenyl) propionate | 0.1 |
| Stabilizer as shown in Table I | 0.3 |

The composition was thoroughly blended in a Brabender Plastograph, and then compression-molded to form sheets 0.5 mm thick. Pieces 2.5 cm square were cut off from the sheets and exposed to a carbon arc in a Weather-O-Meter until failure, to evaluate resistance to deterioration in the presence of ultraviolet light. The time in hours when degradation set in, as determined by a significant discoloration and/or embrittlement, was noted as hours to failure.

Resistance to gas staining was evaluated using nitrogen oxide gas. The sheet was exposed to the gas at 25° C. for 72 hours. Yellowness was measured by a Hunter colorimeter after this exposure.

The results of both tests are given in Table I.

TABLE I

| Example No. | Stabilizer | Resistance To Light Hours to Failure | Resistance to Gas Staining Yellowness |
|---|---|---|---|
| Control 1 | Bis-(2,2,6,6-tetramethyl-4-piperidinyl)sebacate | 470 | 0.14 |
| Control 2 | Tris-(2,2,6,6-tetramethyl-4-piperidinyl)trimellitate | 460 | 0.17 |
| Control 3 | Bis-(9-aza-3-methyl-8,8,10,10-tetramethyl-1,5-diaxaspiro[5,5]-3-undecylmethyl)adipate | 440 | 0.15 |

TABLE I-continued

| Example No. | Stabilizer | Resistance To Light Hours to Failure | Resistance to Gas Staining Yellowness |
|---|---|---|---|
| 1. | (structure with three —CH₂—COO—, CH—COO—, CH₃—CH—COO— groups attached to 2,2,6,6-tetramethylpiperidinyl moieties) | 750 | 0.10 |
| 2. | (structure with three ester groups —CH₂—COO—CH₂—, CH—COO—CH₂—, CH₃—CH—COO—CH₂— attached to 1,4-dioxaspiro tetramethylpiperidinyl moieties with CH₃ substituent) | 720 | 0.09 |
| 3. | (structure with three ester groups —CH₂—COO—CH₂—, CH—COO—CH₂—, CH₃—CH—COO—CH₂— attached to 1,4-dioxaspiro tetramethylpiperidinyl moieties with C₂H₅ substituent) | 740 | 0.10 |

TABLE I-continued

| Example No. | Stabilizer | Resistance To Light Hours to Failure | Resistance to Gas Staining Yellowness |
|---|---|---|---|
| 4. | (structure: three ester groups —CH₂—COO—, —CH—COO—, CH₂=C—COO— each attached to 2,2,6,6-tetramethylpiperidin-4-yl) | 790 | 0.08 |
| 5. | (structure: three ester groups —CH₃—COO—CH₂—, —CH—COO—CH₂—, CH₂=C—COO—CH₂— each attached to a 3-methyl-1,5-dioxaspiro compound with 2,2,6,6-tetramethylpiperidine NH) | 780 | 0.09 |
| 6. | (structure: three ester groups —CH₃—COO—CH₂—, —CH—COO—CH₂—, CH₂=C—COO—CH₂— each attached to a 3-ethyl-1,5-dioxaspiro compound with 2,2,6,6-tetramethylpiperidine NH) | 770 | 0.88 |

It is apparent from the above results that the compounds of the invention are superior stabilizers in enhancing the resistance of the polypropylene polymer composition to deterioration in the presence of ultraviolet light, and to gas staining.

EXAMPLES 7 to 12

High density polyethylene compositions were prepared using stabilizers of the invention and three of the prior art, and having the following formulation:

| Ingredient | Parts by Weight |
| --- | --- |
| High-density polyethylene | 100 |
| Ca-stearate | 1.0 |
| Pentaerythritol tetrakis (β-lauryl mercaptopropionate) | 0.2 |

| Ingredient | Parts by Weight |
| --- | --- |
| 2,6-di-t-butyl-p-cresol | 0.1 |
| Stabilizer as shown in Table II | 0.2 |

The stabilizer was blended with the polymer on a two-roll mill and sheets 0.5 mm thick were prepared by compression molding of the blend. Pieces 2.5 cm square were cut off from the sheets, and exposed in a Weather-O-Meter to ultraviolet light. The time in hours when degradation set in, as determined by a significant discoloration and/or embrittlement, was noted as hours to failure.

Resistance to gas staining was determined using the same test procedure as in Examples 1 to 6.

The results are reported in Table II:

TABLE II

| Example No. | Stabilizer | Resistance To Light Hours to Failure | Resistance to Gas Staining Yellowness |
| --- | --- | --- | --- |
| Control 1 | 2,2,6,6-tetramethyl-4-piperidinyl benzoate | 630 | 0.18 |
| Control 2 | Bis-(9-aza-3-ethyl-8,8,10,10-tetramethyl-1,5-dioxaspiro [5,5]-3-undecyl methyl) sebacate | 810 | 0.16 |
| Control 3 | 2-(2'-hydroxy-5'-methyl-phenyl) benzotriazole | 750 | 0.21 |
| 7. | 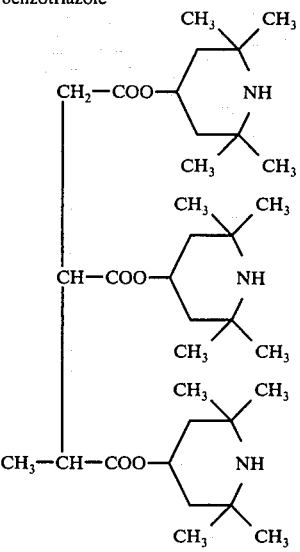 | 1420 | 0.11 |
| 8. | 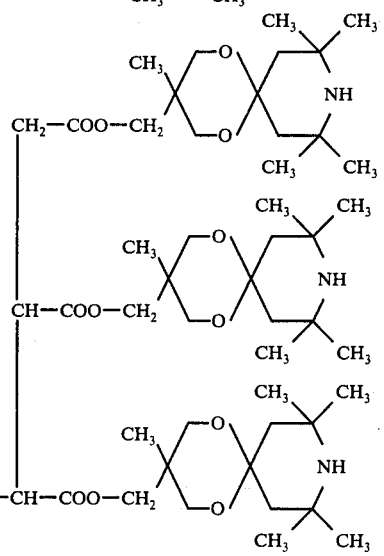 | 1380 | 0.12 |

TABLE II-continued

| Example No. | Stabilizer | Resistance To Light Hours to Failure | Resistance to Gas Staining Yellowness |
|---|---|---|---|
| 9. | (structure) | 1350 | 0.12 |
| 10. | (structure) | 1540 | 0.10 |
| 11. | (structure) | 1490 | 0.11 |

TABLE II-continued

| Example No. | Stabilizer | Resistance To Light Hours to Failure | Resistance to Gas Staining Yellowness |
|---|---|---|---|
| 12. | [structure shown: three repeating units with CH₃—COO—CH₂—, CH—COO—CH₂—, and CH₂=C—COO—CH₂— groups, each attached to a dioxaspiro ring system with C₂H₅ substituent and a 2,2,6,6-tetramethylpiperidinyl NH group] | 1520 | 0.10 |

The stabilizers of the invention are clearly superior to the controls in enhancing resistance of the polyethylene to degradation under ultraviolet light, and to gas staining.

EXAMPLES 13 to 18

Polybutene-1, resin compositions were prepared using stabilizers of the invention and three of the prior art, and having the following formulation:

| Ingredient | Parts by Weight |
|---|---|
| Polybutene-1 | 100 |
| Tetrakis [methylene-3-(3,5-di-t-butyl-4-hydroxyphenyl) propionate] methane | 0.1 |
| Dilauryl thiodipropionate | 0.2 |

| Ingredient | Parts by Weight |
|---|---|
| Stabilizer as shown in Table III | 0.5 |

The stabilizer was blended with the resin in a two-roll mill, and sheets 0.5 mm thick were prepared by compression molding of the resulting blend. Pieces 2.5 cm square were cut off from the sheets, and subjected to ultraviolet light in a Weather-O-Meter. The time in hours when degradation set in, as determined by a significant discoloration and/or embrittlement, was noted as hours to failure.

Resistance to gas staining was determined using the same test procedure as in Examples 1 to 6.

The results are reported in Table III:

TABLE III

| Example No. | Stabilizer | Resistance To Light Hours to Failure | Resistance to Gas Staining Yellowness |
|---|---|---|---|
| Control 1 | 2-hydroxy-4-methoxy benzophenone | 610 | 0.18 |
| Control 2 | Bis-(2,2,6,6-tetramethyl-4-piperidinyl) sebacate | 830 | 0.14 |
| Control 3 | Tris-(9-aza-3-ethyl-8,8,10,10-tetramethyl-1,5-dioxaspiro [5,5]-3-undecylmethyl) trimellitate | 790 | 0.16 |

TABLE III-continued

| Example No. | Stabilizer | Resistance To Light Hours to Failure | Resistance to Gas Staining Yellowness |
|---|---|---|---|
| 13. | (structure: three ester groups —CH₂—COO—, —CH—COO—, CH₃—CH—COO— each linked to 2,2,6,6-tetramethylpiperidin-4-yl (NH)) | 1340 | 0.10 |
| 14. | (structure: three ester groups —CH₂—COO—CH₂—, —CH—COO—CH₂—, CH₃—CH—COO—CH₂— each linked to a methyl-substituted 1,5-dioxaspiro[5.5] ring system bearing 2,2,6,6-tetramethylpiperidinyl NH group) | 1320 | 0.11 |
| 15. | (structure: three ester groups —CH₂—COO—CH₂—, —CH—COO—CH₂—, CH₃—CH—COO—CH₂— each linked to an ethyl-substituted 1,5-dioxaspiro[5.5] ring system bearing 2,2,6,6-tetramethylpiperidinyl NH group) | 1280 | 0.10 |

TABLE III-continued
| Example No. | Stabilizer | Resistance To Light Hours to Failure | Resistance to Gas Staining Yellowness |
|---|---|---|---|
| 16. | 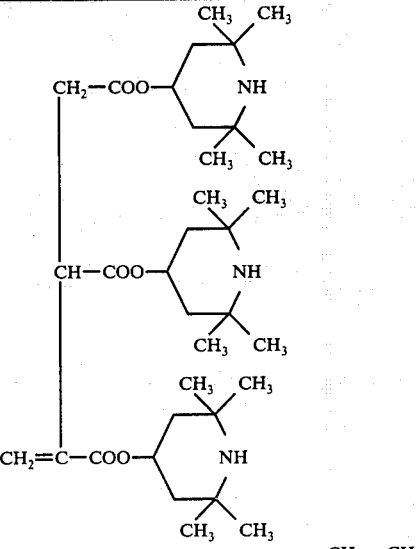 | 1470 | 0.08 |
| 17. | 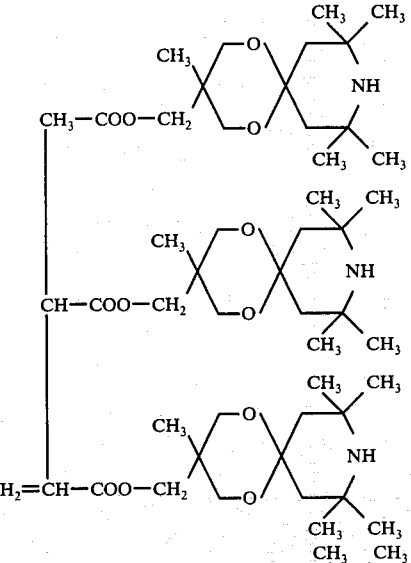 | 1450 | 0.09 |
| 18. | 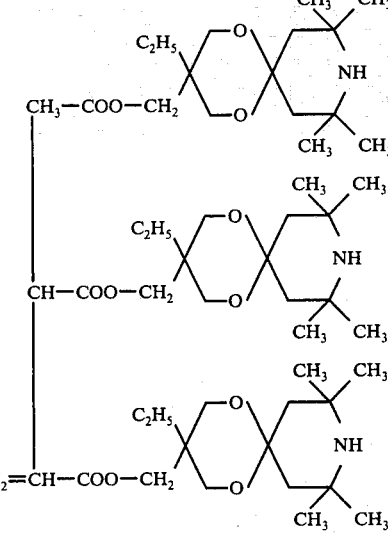 | 1470 | 0.09 |

It is apparent from the data that the stabilizers of the invention are superior to the stabilizers of the prior art in imparting resistance to deterioration under ultraviolet light and to gas staining.

EXAMPLES 19 to 24

A group of polyvinyl chloride resin compositions was prepared having the following formulation:

| Ingredient | Parts by Weight |
|---|---|
| Polyvinyl chloride | 100 |
| Dioctylphthalate | 48 |
| Epoxidized soybean oil | 2.0 |
| Ca stearate | 1.0 |
| Zn stearate | 0.1 |
| Tris-nonylphenyl phosphite | 0.1 |
| Stabilizer as shown in Table IV | 0.1 |

This formulation was blended and sheeted off on a two-roll mill to form sheets 1 mm thick. The light resistance of these sheets was then determined by placing strips 1 cm long in a Weather-O-Meter, and exposing them to ultraviolet light. The time in hours was then noted for the sheet to develop a noticeable discoloration and/or embrittlement, indicating deterioration due to oxidation in the presence of ultraviolet light.

This test was repeated for a total of six stabilizers in accordance with the invention, having the formulae indicated in Table IV, in comparison with three controls. The following results were obtained:

TABLE IV

| Ex. No. | Stabilizer | Hrs. to Failure |
|---|---|---|
| Control 1 | 2-hydroxy-4-octoxybenzophenone | 380 |
| Control 2 | Tris-(9-aza-3-ethyl-8,8,10,10-tetramethyl-1,5-dioxaspiro[5,5]-3-undecylmethyl)trimellitate | 420 |
| Control 3 | 2,2,6,6-tetramethyl-4-piperidinyl stearate | 330 |
| 19. | (structure) | 650 |
| 20. | (structure) | 610 |
| 21. | (structure) | 620 |
| 22. | (structure) | 620 |

TABLE IV-continued

| Ex. No. | Stabilizer | Hrs. to Failure |
|---|---|---|
| 23. | (structure) | 600 |
| 24. | (structure) | 640 |

It is apparent that each of the stabilizers in accordance with the invention is far superior to the controls, which are each conventional ultraviolet light stabilizers for polyvinyl chloride.

Having regard to the foregoing disclosure, the following is claimed as the patentable and inventive embodiments thereof:

1. 2,2,6,6-tetramethyl-4-piperidyl carboxylic acid esters of butane or butene tricarboxylic acids, having the general formula:

$$\begin{array}{c} CH_2-COOR_1 \\ | \\ CH-COOR_1 \\ | \\ R_2=C-COOR_1 \\ | \\ H \end{array}$$

wherein:
$R_1$ is selected from the group consisting of:

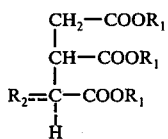
and $R_2$ is selected from the group consisting of $CH_3$ and $CH_2$; and
$R_3$ is lower alkyl having from one to about six carbon atoms.

2. A compound according to claim 1 in which $R_2$ is $CH_3$.
3. A compound according to claim 1 in which $R_2$ is $CH_2$.
4. A compound according to claim 1 in which $R_3$ is $CH_3$.
5. A compound according to claim 1 in which $R_3$ is $C_2H_5$.
6. A compound according to claim 1 in which $R_1$ is 7. A compound according to claim 1 in which $R_1$ is 8. A compound according to claim 1 having the formula:

9. A compound according to claim 1 having the formula:

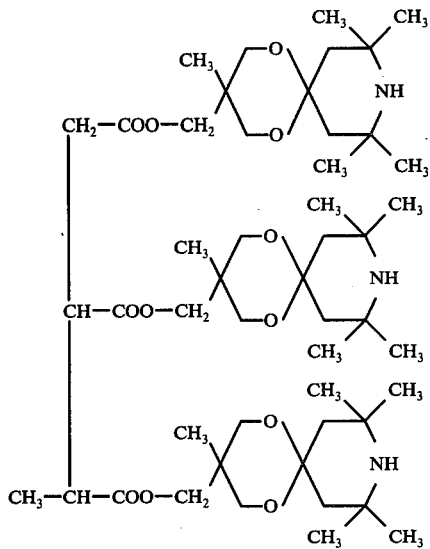

10. A compound according to claim 1 having the formula:

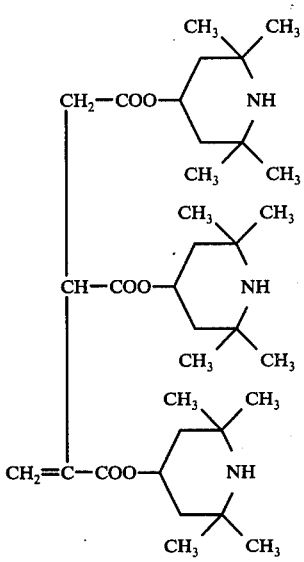

11. A compound according to claim 1 having the formula:

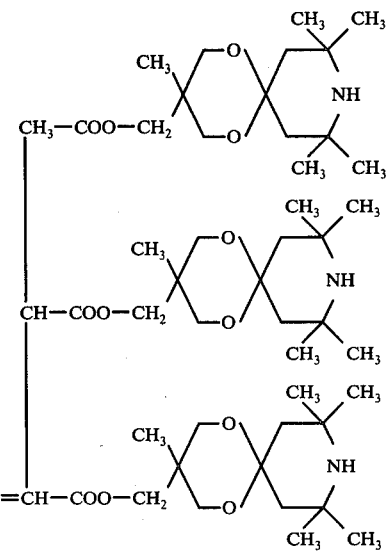

12. A polyvinyl chloride resin composition having improved resistance to deterioration when heated at 350° F., comprising a polyvinyl chloride resin, and a compound in accordance with claim 1.

13. A polyvinyl chloride resin composition in accordance with claim 12, in which the polyvinyl chloride resin is polyvinyl chloride homopolymer.

14. A polyvinyl chloride resin composition in accordance with claim 12, in which the polyvinyl chloride resin is a copolymer of vinyl chloride and vinyl acetate.

15. An olefin polymer composition having improved resistance to deterioration comprising an olefin polymer selected from the group consisting of polymers of alpha-olefins having from two to six carbon atoms and polystyrene, and a compound in accordance with claim 1.

16. An olefin polymer composition in accordance with claim 15 wherein the polyolefin is polypropylene.

17. An olefin polymer composition in accordance with claim 15 wherein the polyolefin is polyethylene.

18. An olefin polymer composition in accordance with claim 15 wherein the polyolefin is polybutene-1.

* * * * *

UNITED STATES PATENT AND TRADEMARK OFFICE
CERTIFICATE OF CORRECTION

PATENT NO. : 4,116,927
DATED : September 26, 1978
INVENTOR(S) : Motonobu Minagawa et al It is certified that error appears in the above-identified patent and that said Letters Patent are hereby corrected as shown below:

Column 1, line 22 :

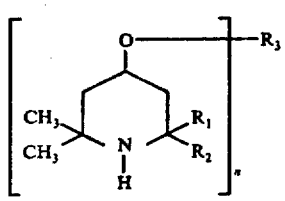

should be

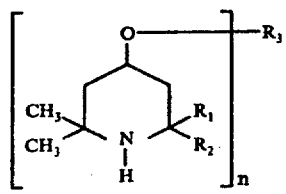

Column 1, line 25 : "Formula" should be --formula--
Column 1, line 66 : "3,893,303" should be --3,898,303--

UNITED STATES PATENT AND TRADEMARK OFFICE
CERTIFICATE OF CORRECTION

PATENT NO. : 4,116,927
DATED : September 26, 1978
INVENTOR(S) : Motonobu Minagawa et al It is certified that error appears in the above-identified patent and that said Letters Patent are hereby corrected as shown below:

Column 2, line 32 :

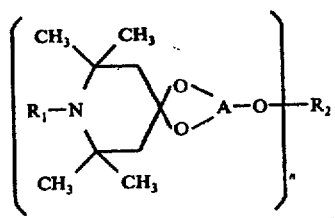

should be

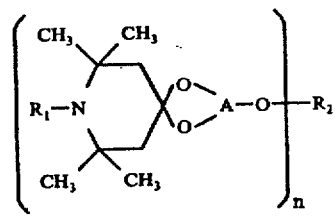

Column 2, line 41 : "When" should be --when--

UNITED STATES PATENT AND TRADEMARK OFFICE
CERTIFICATE OF CORRECTION

PATENT NO. : 4,116,927
DATED : September 26, 1978
INVENTOR(S) : Motonobu Minagawa et al It is certified that error appears in the above-identified patent and that said Letters Patent are hereby corrected as shown below:

Column 3, line 51 :

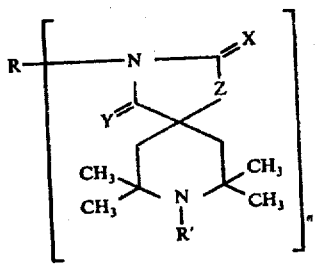

should be

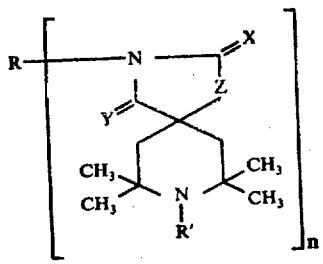

Column 5, line 15 :

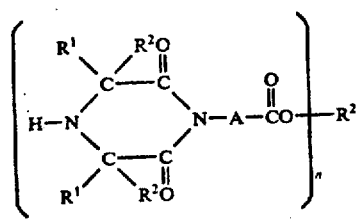

should be

UNITED STATES PATENT AND TRADEMARK OFFICE
CERTIFICATE OF CORRECTION

PATENT NO. : 4,116,927

DATED : September 26, 1978

INVENTOR(S) : Motonobu Minagawa et al

It is certified that error appears in the above-identified patent and that said Letters Patent are hereby corrected as shown below:

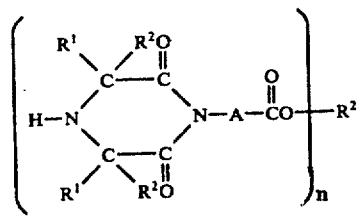

Column 10, lines 42 and 48 :

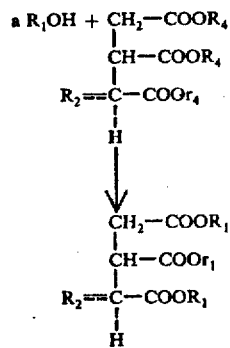

should be

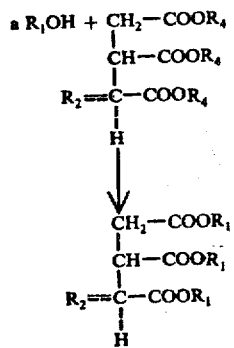

UNITED STATES PATENT AND TRADEMARK OFFICE
CERTIFICATE OF CORRECTION

PATENT NO. : 4,116,927
DATED : September 26, 1978
INVENTOR(S) : Motonobu Minagawa et al It is certified that error appears in the above-identified patent and that said Letters Patent are hereby corrected as shown below:

Column 12, line 49 :

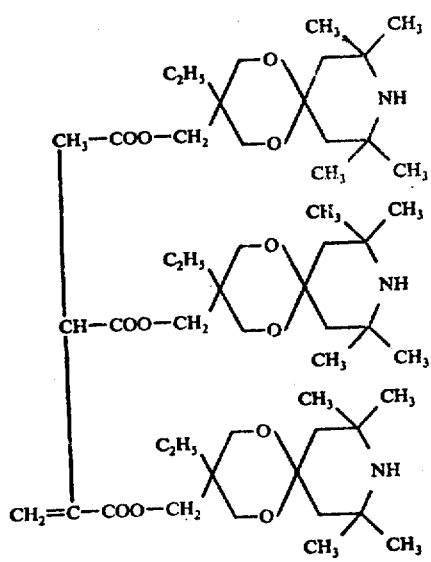 should be 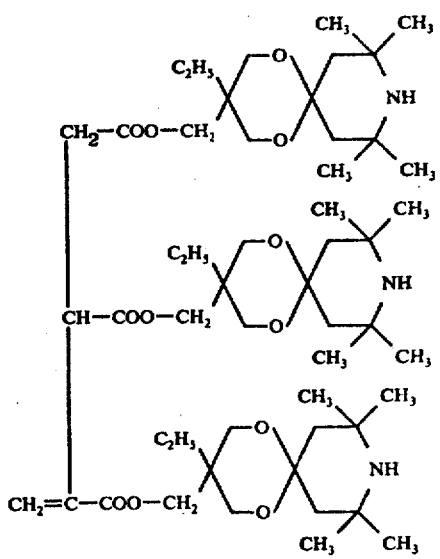

Column 14, Table I,
Control 3, second line : "diaxaspiro" should be --dioxaspiro--.

UNITED STATES PATENT AND TRADEMARK OFFICE
CERTIFICATE OF CORRECTION

PATENT NO. : 4,116,927
DATED : September 26, 1978
INVENTOR(S) : Motonobu Minagawa et al It is certified that error appears in the above-identified patent and that said Letters Patent are hereby corrected as shown below:

Column 21, No. 11, line _____ :

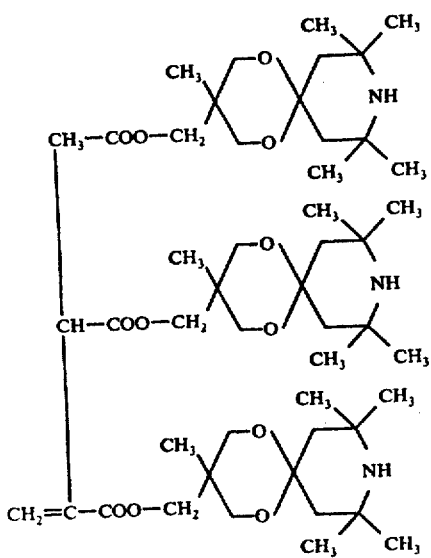

should be

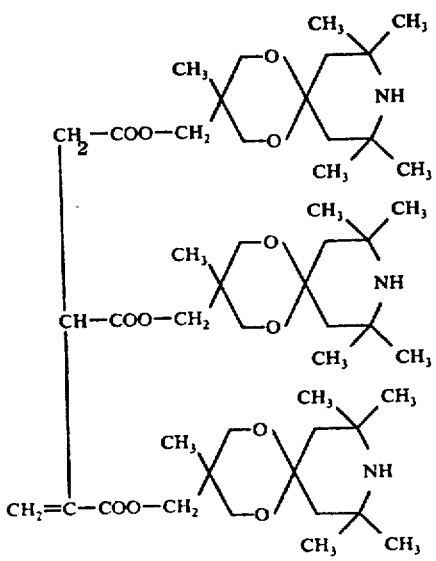

UNITED STATES PATENT AND TRADEMARK OFFICE
CERTIFICATE OF CORRECTION

PATENT NO. : 4,116,927

DATED : September 26, 1978

INVENTOR(S) : Motonobu Minagawa et al

It is certified that error appears in the above-identified patent and that said Letters Patent are hereby corrected as shown below:

Column 23, No. 12, line 4 :

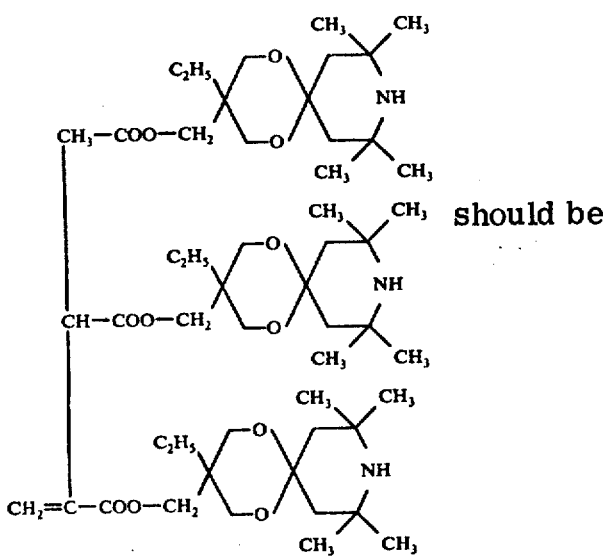 should be 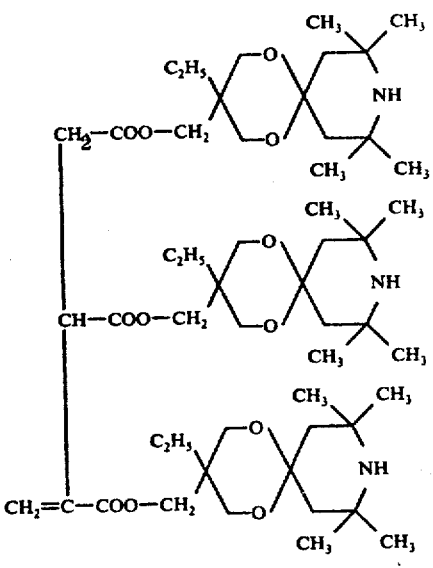

UNITED STATES PATENT AND TRADEMARK OFFICE
CERTIFICATE OF CORRECTION

PATENT NO. : 4,116,927

DATED : September 26, 1978

INVENTOR(S) : Motonobu Minagawa et al

Page 8 of 12

It is certified that error appears in the above-identified patent and that said Letters Patent are hereby corrected as shown below:

Column 27, No. 17,
lines 4 and 14 :

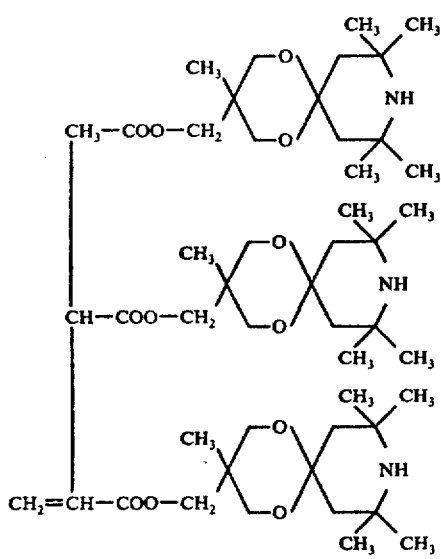 should be 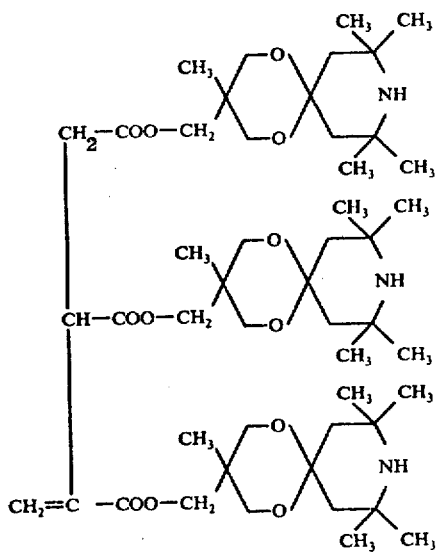

UNITED STATES PATENT AND TRADEMARK OFFICE
CERTIFICATE OF CORRECTION

PATENT NO. : 4,116,927

DATED : September 26, 1978

INVENTOR(S) : Motonobu Minagawa et al

Page 9 of 12

It is certified that error appears in the above-identified patent and that said Letters Patent are hereby corrected as shown below:

Column 27, No. 18, lines 4 and 14 :

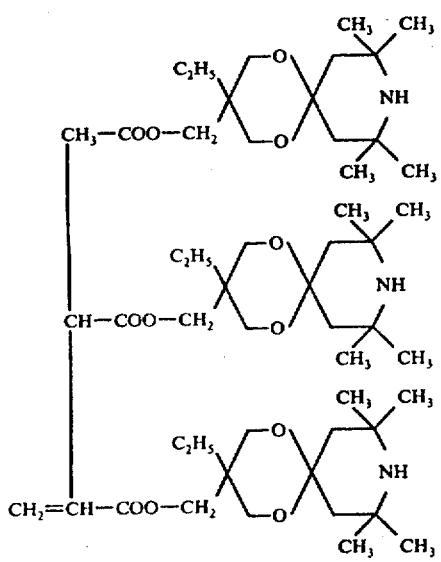 should be 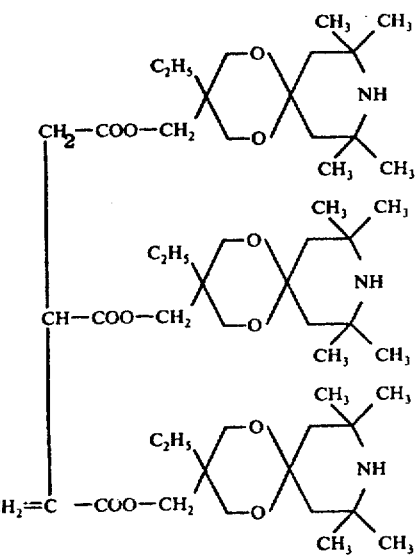

UNITED STATES PATENT AND TRADEMARK OFFICE
CERTIFICATE OF CORRECTION

PATENT NO. : 4,116,927

DATED : September 26, 1978

INVENTOR(S) : Motonobu Minagawa et al

Page 10 of 12

It is certified that error appears in the above-identified patent and that said Letters Patent are hereby corrected as shown below:

Column 31, No. 23, line 10 :

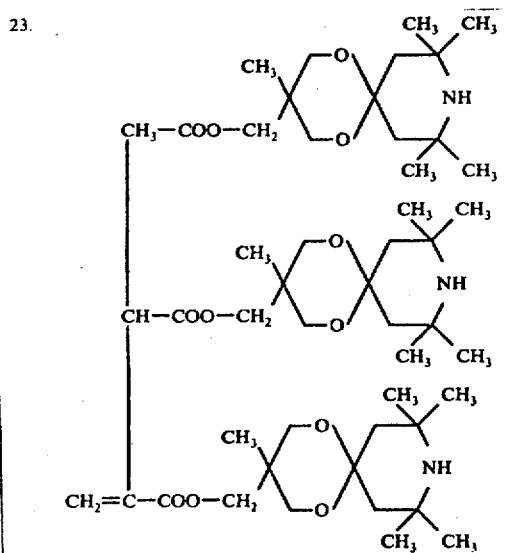

should be

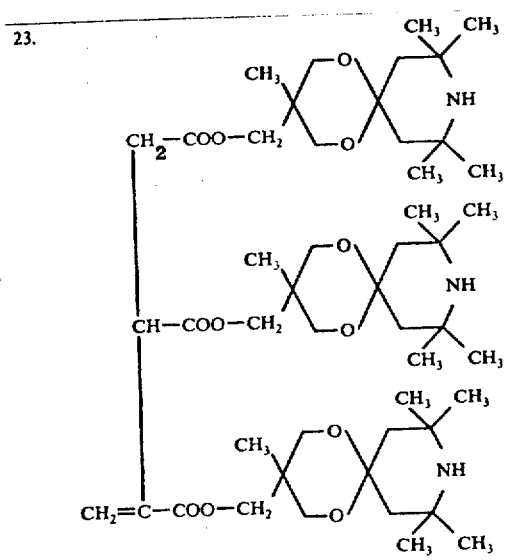

UNITED STATES PATENT AND TRADEMARK OFFICE
CERTIFICATE OF CORRECTION

PATENT NO. : 4,116,927

DATED : September 26, 1978

INVENTOR(S) : Motonobu Minagawa et al

It is certified that error appears in the above-identified patent and that said Letters Patent are hereby corrected as shown below:

Column 31, No. 24
line 31          :

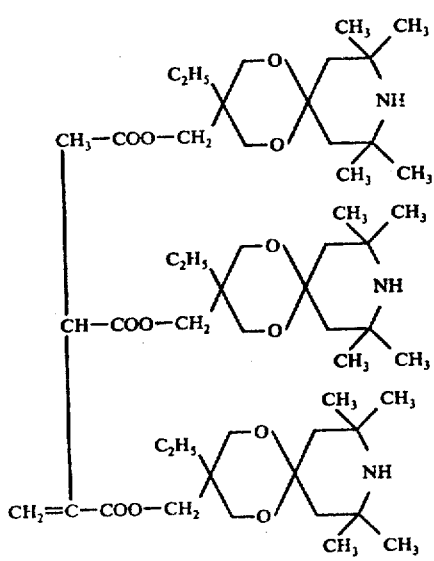  should be  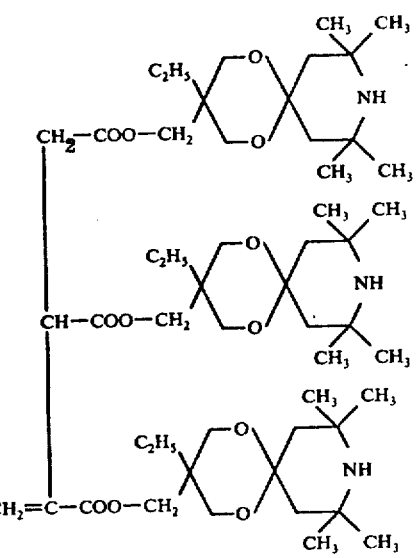

UNITED STATES PATENT AND TRADEMARK OFFICE
CERTIFICATE OF CORRECTION

PATENT NO. : 4,116,927

DATED : September 26, 1978

INVENTOR(S) : Motonobu Minagawa et al

It is certified that error appears in the above-identified patent and that said Letters Patent are hereby corrected as shown below:

Column 34, lines 9 and 22:

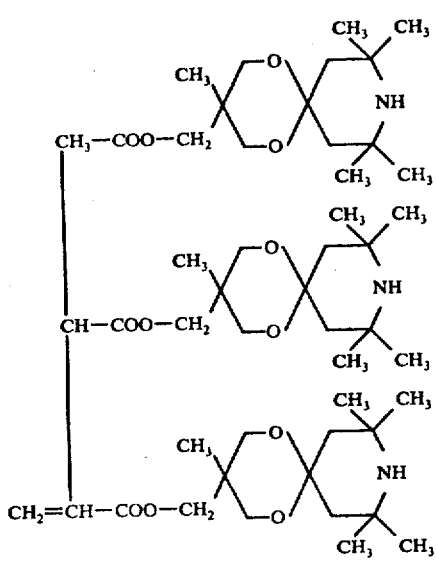 should be 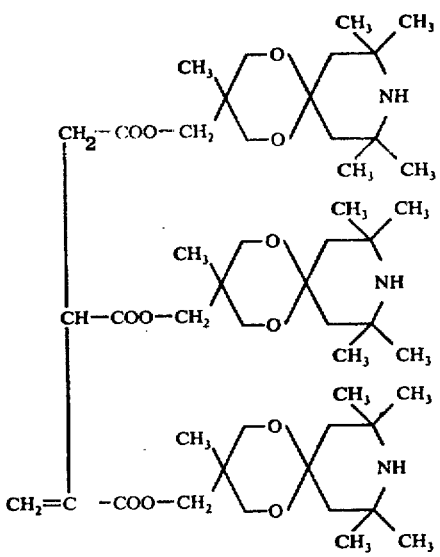

Signed and Sealed this

Twenty-sixth Day of February 1980

[SEAL]

Attest:

SIDNEY A. DIAMOND

Attesting Officer

Commissioner of Patents and Trademarks